United States Patent
Kumar et al.

(10) Patent No.: US 7,649,089 B2
(45) Date of Patent: *Jan. 19, 2010

(54) BIODEGRADABLE OXIDIZED CELLULOSE ESTERS AND THEIR USES AS MICROSPHERES

(75) Inventors: Vijay Kumar, Coralville, IA (US); Yang Dong, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 781 days.

This patent is subject to a terminal disclaimer.

(21) Appl. No.: 10/975,248

(22) Filed: Oct. 28, 2004

(65) Prior Publication Data

US 2005/0131225 A1    Jun. 16, 2005

Related U.S. Application Data

(63) Continuation-in-part of application No. 10/007,866, filed on Dec. 6, 2001.

(60) Provisional application No. 60/514,944, filed on Oct. 28, 2003.

(51) Int. Cl.
  *C08B 3/00*   (2006.01)
  *C08B 3/16*   (2006.01)
  *C08B 3/04*   (2006.01)
  *C08B 3/08*   (2006.01)
  *C08B 3/06*   (2006.01)
  *A61K 31/715* (2006.01)

(52) U.S. Cl. .............. 536/63; 536/64; 536/67; 536/68; 536/69; 536/32; 514/54

(58) Field of Classification Search ............ 536/63, 536/64, 67, 68, 69, 32; 514/54
See application file for complete search history.

(56) References Cited

U.S. PATENT DOCUMENTS

| 2,379,917 | A |   | 7/1945  | Mark et al. |
| 3,501,419 | A | * | 3/1970  | Bridgeford ............... 521/78 |
| 4,590,265 | A |   | 5/1986  | Bohan et al. |
| 5,008,385 | A |   | 4/1991  | Diamantoglou |
| 5,049,395 | A | * | 9/1991  | Chang .................... 424/494 |
| 5,970,988 | A |   | 10/1999 | Buchanan et al. |
| 5,973,139 | A |   | 10/1999 | Lee et al. |
| 5,981,738 | A |   | 11/1999 | Cook et al. |
| 6,368,586 | B1 | * | 4/2002 | Jacob et al. ............ 424/78.08 |
| 6,627,749 | B1 |   | 9/2003 | Kumar |

FOREIGN PATENT DOCUMENTS

| DE | 3346204 A1        | 7/1985 |
| DE | 267 497 A1        | 5/1989 |
| WO | WO 02/053599 A2   | 7/2002 |
| WO | PCT/US2004/036004 | 1/2005 |

OTHER PUBLICATIONS

Chemical Abstracts, vol. 51, No. 1, Jan. 10, 1957, Columbus, Ohio, US; Abstract No. 701g, Toshikazu Fujimura et al., "The acetylation of oxycellulose" XP002210935 Abstract and Chem. High Polymers, vol. 12, 1955, pp. 315-321 XP008007015.

* cited by examiner

*Primary Examiner*—Shaojia Anna Jiang
*Assistant Examiner*—Everett White
(74) *Attorney, Agent, or Firm*—McKee, Voorhees & Sease, P.L.C.

(57) ABSTRACT

A new cellulose excipient, OCCAE, suitable for use as a binder, filler, and/or disintegrant in the development of solid dosage forms and as a bodying agent or a drug carrier in the preparation of topical formulations is described. The cellulose excipient is formed by reacting an oxidized cellulose ester with an alcohol in the presence of a catalyst. The invention also describes the formation of controlled release microspheres using OCCAE and/or oxidized cellulose esters that may be used to control the release of drug in a patient over a time period of several hours to several days.

17 Claims, 9 Drawing Sheets

FT-IR Spectra of OC-14, OCA-14 (DS=2.2), OCAM, and OCAE $^1$H-NMR Spectra of OCA-14 (DS=2.2), OCAM-14, and OCAE-14

$^{13}$C-NMR Spectra of OCA-14 (DS=2.2), OCAM-14, and OCAE-14

Powder XRD Patterns of Cotton Linter, OC-14, OCA-14, OCAM-14, and OCAE-14 pH vs. log $\{(1-\alpha)/\alpha\}$ Plots for OC-14 and OCA-14 (DS=2.2)

Intrinsic Viscosity and Molecular Weight Measurement of OCA-14

Histograms of Diameter Distribution of CPT Microspheres

Powder XRD Patterns of CPT, OCA-CPT, OCAM-CPT, Microspheres

Dissolution/Release Profiles of CPT, OCA-CPT, and OCAM-CPT Microspheres in pH 7.4 PBS at 37.0 °C 1+2F−3(F)^(2/3) Model Fitting for OCAM−CPT Microsphere Release

US 7,649,089 B2

BIODEGRADABLE OXIDIZED CELLULOSE ESTERS AND THEIR USES AS MICROSPHERES

PRIORITY CLAIM

This application is a continuation-in-part application of U.S. patent application Ser. No. 10/007,866 filed Dec. 6, 2001. It also claims priority to U.S. Provisional Application Ser. No. 60/514,944 filed Oct. 28, 2003.

FIELD OF THE INVENTION

This invention relates to biodegradable oxidized cellulose esters, and dosage forms of the same.

BACKGROUND OF THE INVENTION

Oxidized cellulose (6-carboxycellulose, OC) containing 3-25% carboxylic acid groups is a biocompatible, bioresorbable polymer. (See e.g. U.S. Pat. No. 3,364,200). Currently, OC containing 16-24% carboxylic acid groups is used in humans as a hemostatic agent and as a postsurgical adhesion barrier. Despite its widespread use in medicine and related areas, OC has found little use in pharmaceutical applications. This is because it is practically insoluble in water and common organic solvents and, hence, offers little or no formulation flexibility.

Accordingly, it is a primary objective of the present invention to provide novel, biodegradable polymers for potential applications as biodegradable polymers in drug delivery, tissue engineering, and related areas.

It is a further objective of the present invention to provide oxidized cellulose esters, and novel dosage forms of the same.

It is a further objective of the present invention to provide oxidized cellulose carboxylate alkyl esters as a new class of biodegradable polymers.

It is still a further objective of the present invention to provide a method and means of preparing a microsphere dosage form for camptothecin, 5-fluorouracil, and other water soluble or insoluble drugs that provides for effective controlled release of the drug.

The method and means of accomplishing each of the above objectives as well as others will become apparent from the detailed description of the invention which follows hereafter.

SUMMARY OF THE INVENTION

The present invention relates to the use of oxidized cellulose esters (OCE) as a new class of biodegradable polymers for use as biomaterials and as drug carriers in medicine, pharmaceutics, agriculture, and veterinary fields. The invention further relates to the preparation and use of oxidized cellulose carboxylate alkyl/aryl esters (OCCAE) as a new class of biodegradable polymers. OCCAE are prepared by first forming oxidized cellulose esters (OCE). OCE are formed by first treating oxidized cellulose with an organic acid, organic acid/acid anhydride combination, or an organic acid chloride. The OCCAE are then prepared by reacting the OCE with an alcohol in the presence of a carbodiimide coupling agent, and a basic catalyst, such as 4-(dimethylamino)pyridine (DMAP).

The OCE and OCCAE described may be used for a variety of purposes, including entrapment of various water soluble and insoluble drugs to produce controlled release microspheres or other dosage forms, such as gels, implantable devices, tablets, etc. The OCE and/or OCCAE selected will depend upon the time period of drug release desired. In this regard, the nature of alkyl or aryl groups, and their degree of substitution determine their release time. In general, the substitution of a more hydrophobic group and increase in degree of substitution prolong the duration of release.

DETAILED DESCRIPTION OF THE PREFERRED EMBODIMENT

Figure 1:
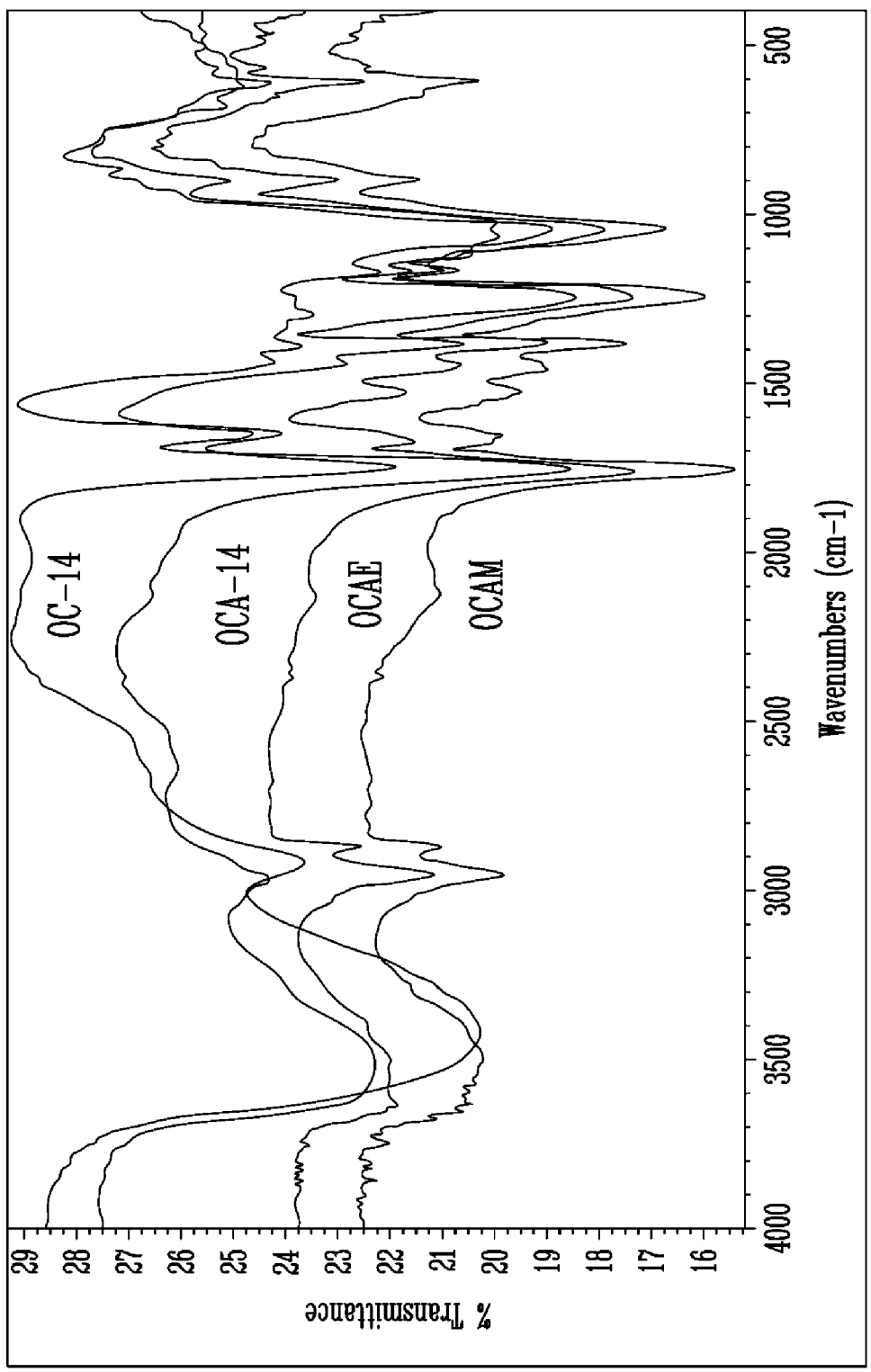
FIG. 1 shows the FT-IR spectra of OC-14, OCA-14 (DS=2.2), OCAM, and OCAE, as described in Example 5.

The present invention relates to the development of novel biodegradable oxidized cellulose esters (OCE) and oxidized cellulose carboxylate alkyl esters (OCCAE). In a previous application, U.S. Ser. No. 10/007,866, the disclosure of which is specifically incorporated herein by reference, the inventors synthesized OCE. These novel modified oxidized celluloses exhibit solubility in aqueous alkaline solution, water, and/or common organic solvents, such as acetone and alcohol, depending on the nature of the ester groups and degree of substitution. The new OCCAE polymers are biodegradable and are useful as biomaterials and as drug carriers.

The present invention also relates to the discovery that OCE may be modified to include an alkyl or an aryl group in place of hydrogen in the carboxylic acid group located on carbon 6, which depending on the degree of substitution and its physical/chemical properties, determines the use of the polymer as a drug carrier or a biomaterial. Thus, the release of drugs from these novel OCCAE polymers is related to the nature of the alkyl/aryl group. The more hydrophobic the group, the slower the release of drug.

The OCE from which the OCCAE of this invention are synthesized have the following general structures I and II:

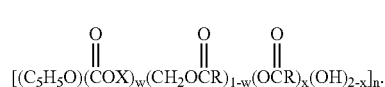

I wherein:

X is H, Na, K, Ca, NH$_4$, or NEt$_3$H;

R is H; CF$_3$; (CH$_2$)$_n$CH$_3$, where n is from 0 to 18, and preferably 0 to 5; (CH$_2$)$_n$COOH, where n is from 1 to 8, and preferably 2 to 4; CY=CZCOOH, where Y and Z are independently selected from the group consisting of hydrogen, methyl, branched alkyl having from 1 to 20 carbon atoms and from one to three cis or trans double bonds; branched alkenyl having from 1 to 20 carbon atoms and having from one to three cis or trans double bonds; CY=CH$_2$, where Y is H, methyl, or phenyl; CH=CHY, where Y is C$_6$H$_5$; CH=CYCOOH, where Y is H or CH$_3$; (CH$_2$)$_8$CH=CH(CH$_2$)$_8$CH$_3$; or C$_6$H$_{(2-6)}$(COOH)$_{0-4}$, CH$_2$CH(COOH)CH$_2$—COOH;

w, is 0.1-1.0;
x is 0.1-2.0; and
n is 30-1500.

and

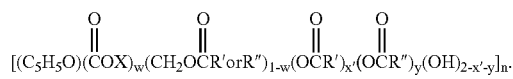

$$[(C_5H_5O)(COX)_w(CH_2OCR' or R'')_{1-w}(OCR')_{x'}(OCR'')_y(OH)_{2-x'-y}]_n.$$

wherein:

X is H, Na, K, Ca, NH$_4$, or NEt$_3$H;

R' and R" are each selected from the group consisting of: H; CF$_3$; (CH$_2$)$_n$CH$_3$, where n is from 0 to 18, preferably 0 to 2; (CH$_2$)$_n$COOH, where n from 1 to 8, preferably 2 to 4; CY=CZCOOH, where Y and Z are independently selected from the group consisting of hydrogen, methyl, branched alkyl having from 1 to 20 carbon atoms and from one to three cis or trans double bonds; branched alkenyl having from 1 to 20 carbon atoms and having from one to three cis or trans double bonds; CY=CH$_2$, where Y is H, methyl, or phenyl; CH=CHY, where Y is C$_6$H$_5$; CH=CYCOOH, where Y is H or CH$_3$; (CH$_2$)$_8$CH=CH(CH$_2$)$_8$CH$_3$; or C$_6$H$_{(2-6)}$(COOH)$_{0-4}$, CH$_2$CH(COOH)CH$_2$—COOH;

w is 0.1-1.0;
x' is 0.1-1.9;
y is 0.1-1.9; and
n is 30-850.

Oxidized cellulose containing at least 3% by weight of carboxylic acid (COOH) content, and preferably 3-25% content, is used as the starting material in the manufacture of the OCE compounds. Various methods of preparing oxidized celluloses are well known in the art, and are described in the following publications, the disclosures of which are hereby expressly incorporated by reference: Heinze et al. (1998); Netherland Patent 77, 111, 034 (1979); U.S. Pat. No. 2,756,112 (1956); U.S. Pat. No. 6,627,749 (2003); Walimbe et al. (1978); C. Bertocchi et al. (1995); E. V. Gert et al. (1995); and Heinze et al. (1993).

The cellulose used in the preparation of oxidized cellulose, the starting cellulose material for OCE, can be from any source, including cotton linters, alpha cellulose, hard and soft wood pulp, regenerated cellulose, amorphous cellulose, low crystallinity cellulose, powdered cellulose, mercerized cellulose, bacterial cellulose and microcrystalline cellulose. Illustrative methods can be found in the following publications, the disclosures of which are hereby incorporated by reference: Powdered cellulose: U.S. Pat. Nos. 4,269,859, 4,438,263, and 6,800,753; Low crystallinity cellulose: U.S. Pat. No. 4,357,467; U.S. Pat. No. 5,674,507; Wei et al. (1996); Microcrystalline cellulose: U.S. Pat. Nos. 2,978,446, 3,146,168, and 3,141,875, Chem Abstr. 111 (8) 59855w, 111 (8) 59787a, 108 (19) 152420y, 104 (22) 188512m, 104 (24) 209374k; CA 104 (24) 193881c, 99 (24) 196859y, 98 (12) 95486y, 94 (9) 64084d, and 85 (8) 48557u.

Prior to treatment in accordance with the methods and solvents of this invention, the oxidized cellulose is preferably treated with a swelling agent for 5-120 minutes, and preferably for about 30-60 minutes, at room temperature. The swelling agent should be used in an amount sufficient to soak the oxidized cellulose. Use of the swelling agent prior to esterification increases the rate of reaction and allows the reaction to occur at a lower temperature (by about 5-25° C.). Further, pretreatment with a swelling agent allows the esterification reaction to be conducted at a lower temperature. Examples of suitable swelling agents include, but are not limited to phosphoric acid, isopropyl alcohol, aqueous zinc chloride solution, water, amines, etc. Following pretreatment, the swelled oxidized cellulose is preferably washed with water, and then with the solvent of the reaction as described below.

The oxidized cellulose source may then be acylated in one of two manners. Method (1) involves treating the cellulose with an organic acid, either alone or in the presence of an acid anhydride. Organic acids and acid anhydrides suitable for this purpose are C$_1$-C$_5$ organic acids and/or anhydrides, with about C$_1$-C$_3$ being preferred. If an anhydride is used, it may be the anhydride corresponding to the organic acid (i.e. acetic acid/acetic anhydride), or a different anhydride. If a non-corresponding anhydride is used, the resulting oxidized cellulose ester product will be a mixed ester. Examples of organic acids that can be used alone include formic acid, trifluroacetic acid, and acetic acid. Examples of organic acids and their corresponding anhydrides include, but are not limited to, acetic acid/acetic anhydride, propionic acid/propionic anhydride, or butyric acid/butyric anhydride, valeric acid/valeric anhydride, caproic acid/caproic anhydride, caprylic acid/caprylic anhydride, nonanoic acid/nonanoic anhydride, capric acid/capric anhydride, lauric acid/lauric anhydride, myristic acid/myristic anhydride, palmitic acid/palmitic anhydride, heptadecanoic acid/heptadecanoic anhydride, stearic acid/stearic anhydride, arachidic acid/arachidic anhydride, behenic acid/behenic anhydride, maleic acid/maleic anhydride, succinic acid/succinic anhydride, mellitic acid/mellitic anhydride, phthallic acid/phthallic anhydride, oleic acid/oleic anhydride, linoleic acid/linoleic anhydride, leinolenic acid/leinolenic anhydride, etc.

In accordance with Method (1), the oxidized cellulose is preferably treated in the presence of an acid catalyst, for e.g. sulfuric acid, o-phosphoric acid, perchloric acid, and zinc chloride solution. If used, the acid catalyst should be present in a concentration ranging from about 0.1-10%, preferably 0.5-2%, by weight of the organic acid anhydride. In general, the higher the reaction temperature the lower the concentration of the acid catalyst, and vice versa, is required.

Method (2) involves treatment of the oxidized cellulose with an excess of an organic acid chloride or organic acid anhydride in an organic solvent such as dimethylsulfoxide (DMSO), N,N'-dimethylacetamide (DMA), N'N'-dimethylformamide (DMF), dioxane, or the like, in the presence of a base catalyst. Appropriate organic acid chlorides are C$_1$-C$_{20}$ compounds, with about C$_1$-C$_{18}$ being preferred. Specific examples of organic acid chlorides include, but are not limited to, caproyl chloride, heptanoyl chloride, octanoyl chloride, capryl chloride, undecanoyl chloride, lauroyl chloride, tridecanoyl chloride, myristoyl chloride, pentadecanoyl chloride, palmitoyl chloride, heptadecanoyl chloride, steroyl chloride, arachidoyl chloride, and behenoyl chloride. Examples of unsaturated acid chlorides include palmitileoyl chloride (cis-9), oleoyl chloride (cis-9), linoleoyl chloride (cis-9,12), linolelaidoyl chloride (trans-9,12), γ-linolenoyl chloride (cis-6,9,12), etc. Examples of unsaturated acids that can be converted to the corresponding acid chlorides by the method known in the art include undecylenic acid, myristoleic acid (cis-9), myristelaidic acid (trans-9), palmitelaidic acid (trans-9), sterolic acid (9-ynoic), etc. Examples of appropriate base catalysts include, but are not limited to pyridine, triethylamine, pyridine derivatives, etc. The amount of the base catalyst that can be used varies from reaction to reaction, typically ranging from 2% to 20% by weight of the amount of the anhydride or acid chloride used in the reaction. In some reactions, it could also be used both as a solvent and as a catalyst.

For both Method (1) and (2), the acylating reaction should occur at a temperature ranging from about 5-125° C., and preferably between about 15-75° C. The reaction should be allowed to continue for a time period of 0.5-12 hours, and preferably between about 2-6 hours. The resulting solid is then preferably filtered, washed with water to a neutral pH range of between about pH 6-8, and then dried using conventional methods such as air-drying, vacuum drying, etc. Yields of the various OCE prepared by these methods range between about 70-95%.

As a general rule, the hydrophobic character of the OCE increases with increasing length of the carbon chain in the ester moiety. For instance, in the free acid form, the OCE are soluble in alcohols, ketones, aqueous alcohol, aqueous acetone, DMSO, DMA, DMF, or mixtures thereof. Owing to the presence of free carboxylic groups, OCE are soluble in mild to strong aqueous alkali solutions. The pH at which the dissolution occurs depends on the nature of the ester moiety present in the polymer and degree of substitution. For example, oxidized cellulose acetate is insoluble in water and acidic aqueous solutions, but swells in pH 7 and higher buffer solutions, and eventually dissolves.

In comparison, oxidized cellulose maleate or other unsaturated alkyl or alkenyl substituted esters containing one or more free carboxylic groups on the ester moiety as pendant groups hydrate in water and dissolve to give a viscous solution. The aryl substituted esters of oxidized cellulose, irrespective of the absence or presence of the free carboxylic group, neither swell nor dissolve in water. They are insoluble in acidic aqueous solutions, but dissolve in mild to strong aqueous alkaline solutions. They are soluble in alcohol, acetone, and a variety of other simple and mixed organic solvents. The mixed oxidized cellulose esters exhibit solubility intermediate to those of the parent alkyl and aryl cellulose esters.

Once formed, the OCE are reacted with an alcohol. Any $C_1$-$C_1$-6 alcohol may be used for this purpose, ultimately depending on the length of the alkyl chain or aryl group desired. Alcohol can be used in excess. Temperature is not critical in this step, and the reaction can occur in a broad range from about −5° C. to as high as the boiling/melting point of the alcohol being used. For cost and practical reasons, room temperature is preferred.

Prior to reaction with the alcohol, the OCE is dissolved in an organic solvent. Any organic solvent will work for this purpose so long as it is effective in dissolving the OCE and does not contain a hydroxyl or carboxylic acid group. Examples of appropriate organic solvents for this purpose include, but are not limited to, halogenated aliphatic hydrocarbons and methylene dichloride. Persons skilled in the art can readily determine an appropriate organic solvent for this purpose. Once the OCE is dissolved, the alcohol is added in excess.

A carbodiimide coupling agent and a basic catalyst (what concentrations?), as solids or as solutions in the reaction solvent, are then added. The amount of OCE to carbodiimide should range from about 1:0.1 to about 0.1-10 OCE to carbodiimide, with a range of about 1:0.5-1:3 being preferred. Any carbodiimide may be used as a coupling agent including, but not limited to, (S)-1,1'-binaphthyl-2,2'-diylcarbodiimide, bis[(S)-1,1'-binaphthyl-2,2'-diyl]bis(carbodiimide), 2,2'-biphenylenecarbodiimide, bis(2,2'-biphenylene)bis(carbodiimide), and 1,3-dicyclohexylcarbodiimide (DCC), with DCC being preferred. Any basic catalyst will work for purposes of this step including, but not limited to, magnesium oxide, calcium oxide, mixed oxides obtained by calcination of layered double hydroxides, zeolites, hydrotalcites, and 4-(dimethylamino) pyridine (DMAP). Persons skilled in the art are well familiar with such catalysts. The preferred basic catalyst is DMAP. The amount of coupling agent to catalyst is not critical, except that at least a slight excess of coupling agent should be used. A range of about 2:1-10:1 coupling agent to catalyst is preferred. The mixture is preferably stirred for a period of time sufficient to produce the desired OCCAE. This time period from about 15 minutes to about 48 hours, and preferably about 4-24 hours.

The resulting OCCAE may be used for the same purposes and in the same manner as OCE, i.e. as biomaterials and as drug carriers in medicine, pharmaceutics, agriculture, and veterinary fields. Both OCE and OCCAE may be used in the manufacture of sustained release dosage forms, such as granules, microspheres, tablets, capsules, gels, etc. They can be used as coating materials.

The formulation of pharmaceutically-acceptable dosage forms is well known in the art. As used herein, the term "pharmaceutically-acceptable" refers to the fact that the preparation is compatible with the other ingredients of the formulation and is safe for administration to humans and animals.

Oral dosage forms encompass tablets, capsules, and granules. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, dissolving, and lyophilizing processes. The processes to be used will depend ultimately on the physical properties of the active ingredient used.

Suitable excipients are, in particular, fillers such as sugars for example, lactose or sucrose, mannitol, sorbitol, cellulose, and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone, and powdered oxidized cellulose as described in U.S. Pat. No. 6,627,749. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures.

The microspheres of this invention may be generally prepared by conventional emulsion/solvent evaporation method by suspending/dissolving the drug in an appropriate solvent system in an amount sufficient to suspend/dissolve the drug being used. Such solvent systems for particular types of drugs are well known in the art. For example, for purposes of camptothecin, a 4:1 ratio of dichloromethane/methanol is preferred, while dichloromethane is preferred for 5-fluorouracil (5-FU).

The drug suspension/solution is then combined with a solution of OCE, OCCAE, or OCE/OCCAE mixture (drug concentration of about 1-10%) in the same solvent system, which is then added dropwise to an aqueous solution containing an emulsifying agent. Appropriate emulsifying agents include without limitation various emulsifiers, surfactants, and wetting agents known in the pharmaceutical arts, such as polyvinylalcohol, sodium lauryl sulfate, dodecyl sodium sulfate, docusate salts such as the sodium salt thereof, alkyl carboxylates, acyl lactylates, alkyl ether carboxylates, N-acyl sarcosinates, polyvalent alkyl carbonates, N-acyl glutamates, fatty acid, polypeptide condensates, sulfuric acid esters, nonionic surfactants and/or cationic surfactants such as, for example, polyoxyethylene compounds, lecithin, ethoxylated alcohols, ethoxylated esters, ethoxylated amides, polyoxypropylene compounds, propoxylated alcohols, ethoxylated/propoxylated block polymers, propoxylated esters, alkanolamides, amine oxides, fatty acid esters of polyhydric alcohols, ethylene glycol esters, diethylene glycol esters, propylene glycol esters, glycerol esters, polyglycerol fatty acid esters, SPAN's (e.g., sorbitan esters), TWEEN's (i.e., sucrose esters), glucose (dextrose) esters and simethicone. Other suitable pharmaceutically-acceptable surfactants include acacia, benzalkonium chloride, cholesterol, emulsifying wax, glycerol monostearate, lanolin alcohols, lecithin, poloxamer, polyoxyethylene, and castor oil derivatives. A 1% solution of polyvinylalcohol (PVA) is preferred.

The mixture is stirred with vigorous agitation to form an O/W emulsion. The agitation is continued for a period of time sufficient to form microspheres, which are formed as the organic solvent is evaporated. This time period will generally range from about 0.5-48 hours. The temperature at which this occurs will depend upon the temperature necessary to evaporate the organic solvent chosen. The amount and vigor of the stirring will determine the size of the microspheres formed, which can range in size from micrometers to nanometers in diameter. The microspheres are then filtered and dried. Double emulsion and other conventional formulation methods can also be used to prepare microspheres in accordance with this invention.

Microspheres that include OCE will release drug over a time period of between about 24-150 hours, depending on the degree of oxidation, i.e. carboxylic acid content and the nature of the ester group. Microsphere formulations that include OCCAE will release drug over a much longer time period of between about 150 hours to 6 months or longer, again depending on the nature of drug, the types of ester groups, and/or degree of substitution of alkyl or aryl-substituted carboxylic acid ester group. Thus, a drug dosing strategy can be formed depending on the drug release time desired by selecting a particular OCE, OCCAE, or combination of the two types of polymers, to achieve this result. A higher proportion of OCE in the microsphere will provide a faster release of drug because of increased hydrophilicity. Likewise, a higher proportion of OCCAE in the microsphere will provide a slower release of drug because of increased hydrophobicity.

The OCCAE of this invention have the following general structures I and II:

$$[(C_5H_5O)(COX)_w(CH_2OCR)_{1-w}(OCR)_x(OH)_{2-x}]_n. \quad\quad I$$

wherein:

X is H, alkyl ($C_1$-$C_{16}$) or an aryl group;

R is H; $CF_3$; $(CH_2)_nCH_3$, where n is from 0 to 18, and preferably 0 to 5; $(CH_2)_nCOOH$, where n is from 1 to 8, and preferably 2 to 4; CY=CZCOOH, where Y and Z are independently selected from the group consisting of hydrogen, methyl, branched alkyl having from 1 to 20 carbon atoms and from one to three cis or trans double bonds; branched alkenyl having from 1 to 20 carbon atoms and having from one to three cis or trans double bonds; CY=$CH_2$, where Y is H, methyl, or phenyl; CH=CHY, where Y is $C_6H_5$; CH=CYCOOH, where Y is H or $CH_3$; $(CH_2)_gCH$=CH$(CH_2)_8CH_3$; or $C_6H_{(2-6)}(COOH)_{0-4}$, $CH_2CH(COOH)CH_2$—COOH;

w, is 0.1-1.0;

x is 0.1-2.0; and n is 30-1500.

and $$[(C_5H_5O)(COX)_w(CH_2OCR' or R'')_{1-w}(OCR')_{x'}(OCR'')_y(OH)_{2-x'-y}]_n. \quad\quad II$$

wherein:

X is H, alkyl ($C_1$-$C_{16}$) or an aryl group;

R' and R" are each selected from the group consisting of: H; $CF_3$; $(CH_2)_nCH_3$, where n is from 0 to 18, preferably 0 to 2; $(CH_2)_nCOOH$, where n from 1 to 8, preferably 2 to 4; CY=CZCOOH, where Y and Z are independently selected from the group consisting of hydrogen, methyl, branched alkyl having from 1 to 20 carbon atoms and from one to three cis or trans double bonds; branched alkenyl having from 1 to 20 carbon atoms and having from one to three cis or trans double bonds; CY—$CH_2$, where Y is H, methyl, or phenyl; CH=CHY, where Y is $C_6H_5$; CH=CYCOOH, where Y is H or $CH_3$; $(CH_2)_8CH$=CH$(CH_2)_8CH_3$; or $C_6H_{(2-6)}(COOH)_{0-4}$, $CH_2CH(COOH)CH_2$—COOH;

w is 0.1-1.0;

x' is 0.1-1.9;

y is 0.1-1.9; and n is 30-850.

The new OCCAE is nearly amorphous. Like OCE, it is soluble in common organic solvents. In contrast, oxidized cellulose can only be dissolved in alkaline aqueous solutions. The carboxylic acid content of OCCAE is significantly reduced compared to oxidized cellulose and OCE, indicating the substitution of carboxylic acid group to carboxylic alkyl or aryl ester group. The carboxylic content of OCCAE will depend upon the degree of substitution of the carboxylic acid alkyl or aryl ester group, but is generally much lower than for OCE.

The degree of polymerization (DP) of the new product was determined according to the procedure described in the U.S.

Pharmacopeia/National Formulary (USP 24/NF 19), page 2432. The value ranged between 25 and 750.

The following examples are provided to illustrate but not limit the invention. Thus, they are presented with the understanding that various modifications may be made and still be within the spirit of the invention.

Example 1

Preparation of Oxidized Cellulose Acetate Alkyl Esters

Materials

The starting material oxidized cellulose acetate (OCA) was prepared from oxidized cellulose (OC) by treatment with a mixture of acetic acid and acetic acid anhydride in the presence of catalytic amounts of concentrated sulfuric acid, in accordance with U.S. Ser. No. 10/007,866, filed Dec. 6, 2001. OC was prepared from a reaction between cotton linter sheet (Grade R 270; Southern Cellulose Products, Inc., Chattanooga, Tenn.) and a mixture of phosphoric acid (85% w/w), nitric acid (69.9% w/w) and sodium nitrite at room temperature for different time periods (See U.S. Pat. No. 6,627,749, Sep. 30, 2003, the disclosure of which is herein specifically incorporated by reference.

1,3-dicyclohexylcarbodiimide (DCC) and 4-(dimethylamino)pyridine (DMAP) were obtained from Aldrich Chemical Co. (Milwaukee, Wis.) and used as a coupling agent and as a catalyst, respectively.

Methods

Synthesis of Methyl Ester of Oxidized Cellulose Acetate (OCAM-14)

20 g of dried OCA-14 was dissolved in 240 ml of a 1:1 (v/v) mixture $CH_2Cl_2$:$CH_3OH$. To this solution, 13.0 g of DCC and 1.3 g of DMAP were added. The reaction mixture was stirred at room temperature for 24 hours and then filtered. The solid collected was first washed with hexane (3×100 ml) and then with methanol (3×50 ml). It was dried in a vacuum oven at 50° C. for 12 hours.

Synthesis of Butyl Ester of Oxidized Cellulose Acetate (OCABUT-14)

20 g of dried OCA-14, 22 g of DCC, and 2.2 g of DMAP were dissolved in 240 ml of a 2:1 (v/v) mixture of $CH_2Cl_2$: butanol. The mixture was stirred at room temperature for 24 hours. The residue that formed was filtered, washed with hexane (3×100 ml) and then with 3×50 ml with methanol. The product was dried in a vacuum oven at 50° C. for 12 hours.

Synthesis of Cetyl Ester of Oxidized Cellulose Acetate (OCACET-14)

To a solution of dried OCA-14 (10 g) in 120 ml of acetone, 15.0 g of cetyl alcohol was added. After cetyl alcohol was dissolved, 10.0 g of DCC and 1.0 g of DMAP were added. The reaction mixture was stirred at room temperature for 24 hours. The residue that formed was first washed with hexane (3×100 ml) and then with 3×50 ml of methanol. The resulting product was dried in a vacuum oven at 50° C. for 12 hours.

Synthesis of Methyl Ester of Oxidized Cellulose Acetate (OCAM-20)

30 g of dried OCA-20 (0.13 mol) was dissolved in 300 ml of a 1:1 (v/v) mixture of $CH_2Cl_2$:$CH_3OH$. DCC (48 g) and DMAP (4.8 g) were dissolved in 300 ml of the same solvent mixture and then added to the OCA-20 solution over a period of 1 hour. The mixture was stirred at room temperature for 6 hours. The solvent of the mixture was removed on a rotary evaporator under reduced pressure. The solid obtained was washed first with hexane (3×200 ml) and then with 3×100 ml of methanol. The resulting product was dried in a vacuum oven at 50° C. for 12 hours.

Synthesis of Octyl Ester Derivative of Oxidized Cellulose Acetate (OCAOCT-20)

30 g of dried OCA-20 (0.13 mol) was dissolved in 600 ml of a 2:1 (v/v) mixture of acetone and octanol. To this solution, 50 g of DCC and 5 g of DMAP were added. The reaction mixture was at room temperature for 24 hours. The excess solvents from the reaction mixture were removed on a rotary evaporator under reduced pressure. The solid obtained was washed with hexane (3×200 ml) and then with 3×100 ml of methanol. The resulting product was dried in a vacuum oven at 50° C. for 12 hours.

Synthesis of Cetyl Ester Derivative of Oxidized Cellulose Acetate (OCACET-20)

30 g of dried OCA-20 (0.13 mol) was dissolved in 500 ml of a 1:4 mixture of $CH_2Cl_2$ and acetone. 35 g of cetyl alcohol, followed by 50 g. of DCC and 5 g of DMAP, were then dissolved in the OCA-20 solution. The reaction mixture was stirred at room temperature for 24 hours. The solvents of the mixture were removed on a rotary evaporator under reduced pressure. The solid obtained was washed with hexane (3×100 ml) and then with 3×50 ml of methanol. The resulting product was dried in a vacuum oven at 50° C. for 12 hours.

Results and Discussion

Preparation and Characterization of OCA Alkyl Esters

The preparation of alkyl esters of OCA was achieved by reacting OCA with an alcohol using dicyclohexylcarbodiimide DCC as a coupling agent and DMAP as a catalyst at room temperature. DCC has been extensively used in the coupling of amines and carboxylic acids in peptide and protein chemistry. It has also been found to be a useful agent in the acylation of an alcohol, when combined with DMAP. The use of DMAP in the reaction is very important because the reaction in the absence of DMAP proceeds to completion slowly and often produces byproducts. In these examples, the ratio of DCC and DMAP was fixed (DCC:DMAP=10:1, w/w). However, any ratio in this regard may be used. DMAP was added first to the reaction mixture and then DCC was slowly added drop-wise to the solution. DMAP facilitates the conversion of the activated OCE-DCC complex intermediate into the DMAP-OCE intermediate, which is then attacked by the alcohol to give the product.

The FT-IR spectra of OCA-20 and OCAM-20 products formed after 2, 6, 18, and 48 hours of reaction time was determined. OCAM-20 prepared after 2 hr. showed only a slight decrease in the intensity of the $\nu$(O—H) vibration band in the region between 2500 and 3500 $cm^{-1}$ compared to the corresponding peak in the spectrum of OCA-20. This peak, however, is less intense for OCA products prepared after 6, 18 and 48 hours, suggesting that a decrease in the carboxylic acid content in the products with increasing time. Another notable feature in the spectra of OCAM-20 products is that the $\nu$(C—H) vibration bands appearing in the region between 2850 $cm^{-1}$ and 2950 $cm^{-1}$ show significantly increased intensity compared to the corresponding peaks in the spectrum for OCA-20. The presence of a strong band at 1750 $cm^{-1}$ in the spectra of OCAM-20 is attributed to cell-O—C(O)—$CH_3$ and Cell-C(O)—O—$CH_3$. In OC, the carbonyl peak of carboxylic acid groups is identified at 1734 $cm^{-1}$. However, in the spectrum of OCA (reaction time 0 h), the peaks due to cell-C(O)—OH and Cell-O—C(O)—$CH_3$ overlap and appear at about 1750 $cm^{-1}$. The strong bands appearing at 1060 cm$^{-1}$ and 1240 cm$^{-1}$ in the spectra of OCA-20 and OCAM-20 are assigned to ν(C—O) vibration.

The $^1$H-NMR spectra of OCA-20 and OCAM-20 products prepared using 2, 6, 18, and 48 h of reaction time were also determined. Protons bonded to the ring carbons appear at 3.5-6.0 ppm, and those of acetyl groups at 1.5-2.3 ppm. The protons from C$\underline{H}_3$O— and —C$\underline{H}_2$O— occur at ~3.7 ppm.

In the $^{13}$C-NMR spectra, the peaks at 100.4, 71.7, 72.4, 72.7, 76.0, and 63.4 ppm are attributed to C1, C2, C3, C4, C5, and C6, respectively. The peak at ~170 ppm is due to carbonyl carbons belonging to the acetyl and carboxyl acid groups. The peaks at 53.4 ppm and 61.3 ppm belong to $\underline{C}$H$_3$O— and —$\underline{C}$H$_2$O— carbons. The methyl carbon in the ethyl group is identified at 14.1 ppm.

Example 2

Preparation of OCA and OCA Alkyl Ester-Camptothecin Microspheres

Experimental Section

Reduction of the Drug Particle Size

The particle size of pure camptothecin (CPT) and 5-fluorouracil (5-FU) was reduced by grinding the drug with a pestle and mortar gently.

Preparation of OCA 14-Camptothecin Microspheres

About 200 mg of CPT was accurately weighed and suspended in 70 ml of a 6:1 (v/v) mixture of methylene dichloride:methanol. To this, 2.5 g of OCA-14 was added. The mixture was stirred until OCA-14 completely dissolved in the solution. The resulting solution was then added drop-wise using a syringe over a period of 15 minutes to 300 ml of 1% (w/v) solution of poly(vinyl alcohol) (PVA) in water with vigorous stirring (~715 r.p.m.) at room temperature. The stirring was continued at the same speed for an additional 5 minutes. The mixture was then allowed to stir at a slower speed (~30 r.p.m.) for 4 hours to remove the organic solvents. The microspheres formed were separated by filtration, washed with 3×50 ml distilled water and then dried under vacuum (25 inches Hg) at 50° C. for 12 hours.

Preparation of OCAM14-Camptothecin Microspheres

The preparation of OCAM14-CPT microspheres was achieved following the same procedure as described in above section, except for that the amounts of CPT and OCAM employed in the experiment were 40 mg and 450 mg, respectively, and they were dissolved in 10 ml of a 8:2 (v/v) mixture of methylene chloride:methanol. The emulsion was prepared using 100 ml of 1% (w/v) aqueous PVA solution and an agitation rate of 400 r.p.m. The mixture was then allowed to stir at a slow speed (~200 r.p.m.) for 4 hours. The microspheres formed were separated by filtration, washed with 3×50 ml distilled water and then dried under vacuum at 50° C. for 12 hours.

Preparation of OCA14-OCAM14 (1:1)-Camptothecin Microspheres

The preparation of OCA14-OCAM14 (1:1)-CPT microspheres was achieved following the same procedure as described in above section, the amount of CPT is 30.0 mg, and OCA14 and OCAM14 employed in the experiment were 200 mg and 200 mg. They were dissolved in 10 ml of a 8:2 (v/v) mixture of methylene chloride:methanol. The emulsion was prepared using 100 ml of 1% (w/v) aqueous PVA solution and an agitation rate of 400 r.p.m. The mixture was then allowed to stir at a slow speed (~200 r.p.m.) for 4 hours. The microspheres formed were separated by filtration, washed with 3×50 ml distilled water and then dried under vacuum at 50° C. for 12 hours.

Preparation of OCAM20-Camptothecin Microspheres

About 1 g of CPT which particle size had been reduced was accurately weighed and suspended in 20 ml of methylene dichloride:methanol (8:2). To this mixture, 2.0 g of OCA-20 was added. The mixture was stirred until OCAM20 completely dissolved in the solution. The resulting solution was then added drop-wise using a syringe to 300 ml of 1% (w/v) solution of poly(vinyl alcohol) (PVA) in water with vigorous stirring (~400 r.p.m.) at room temperature. The stirring was continued at the same speed for an additional 5 minutes. The mixture was then allowed to stir at a slower speed (~200 r.p.m.) for 4 hours to remove the organic solvents. The microspheres formed were separated by filtration, washed with 3×50 ml distilled water and then dried under vacuum at 50° C. for 12 hours.

Preparation of OCAM20-OCA20 (1:1)-Camptothecin Microspheres

About 1 g of CPT which particle size had been reduced was accurately weighed and suspended in 20 ml of methylene dichloride:methanol (8:2). To this mixture, 1.0 g of OCAM20 and 1.0 g of OCA20 were added. The mixture was stirred until OCA20 and OCAM20 completely dissolved in the solution. The resulting solution was then added drop-wise using a syringe to 200 ml of 1% (w/v) solution of poly(vinyl alcohol) (PVA) in water with vigorous stirring (~400 r.p.m.) at room temperature. The stirring was continued at the same speed for an additional 5 minutes. The mixture was then allowed to stir at a slower speed (~200 r.p.m.) for 4 hours to remove the organic solvents. The microspheres formed were separated by filtration, washed with 3×50 ml distilled water and then dried under vacuum at 50° C. for 12 hours.

Example 3

Preparation and Characterization of OCA Alkyl Ester 5-FU Microspheres

5-Fluorouracil (5-FU) was introduced 30 years ago as a synthesized anticancer agent. It still continues to be widely used in the treatment of several common malignancies including colon cancer, breast cancer, and skin cancer. It is an analog of the naturally occurring pyrimidine uracil. It is more acidic than its natural pyrimidine analog and is also more soluble in aqueous solutions. It is stable in solution at physiological pH for weeks. It is a poorly absorbed drug after oral administration with erratic bioavailability. The parenteral preparation is the major dosage form, used intravenously (bolus or continuous infusion). After parenteral administration of 5-fluorouracil, there is a rapid distribution of the drug and rapid elimination with an apparent terminal half-life of approximately 8 to 20 minutes. In order to maintain therapeutic concentrations of the drug in the blood, long term infusion has thusfar been preferred.

To evaluate the use of oxidized cellulose esters as drug carriers for water soluble drugs, 5-fluorouracil was chosen as a model drug. Oxidized cellulose esters containing methyl, octyl, and cetyl substituted carboxylic acid ester groups were used to study the substitution effect on the release characteristics of the drug. The release studies were performed in pH 7.4 phosphate buffer-saline (PBS) solution (ionic strength ~0.165 M).

Preparation of OCAM20, OCAOCT20, and OCACET20—5 FU Microspheres

About 1.0 g of 5-fluorouracil with reduced particle size was accurately weighed and suspended in 10.0 ml of methylene dichloride. To this mixture, 1.0 g of polymer (OCAM20, OCAOCT20, or OCACET20) was added. The mixture was stirred until the polymer completely dissolved in the solution. The resulting solution was then added drop-wise using a syringe to 50 ml of 1% (w/v) solution of poly(vinyl alcohol) (PVA) in water with vigorous stirring (~400 r.p.m.) at room temperature. The mixture was then allowed to stir at a slower speed (~200 r.p.m.) to remove the organic solvents. The microspheres formed were separated by filtration, washed with 3×50 ml distilled water and then dried under vacuum at 50° C. for 12 hours.

The drug loading and drug loading efficiencies are presented in Table 1.

TABLE 1

Drug Content of OCA Ester-5-fluorouracil and Their Drug Loading Efficiency

| Sample | Drug Content (%, w/w) | Loading Efficiency |
|---|---|---|
| OCAM20-5FL | 12.65 (±0.53) | 42.2% |
| OCAOCT-5FL | 11.24 (±0.61) | 37.5% |
| OCACET-5FL | 8.97 (±1.11) | 29.9% |

Morphology of 5-fluorouracil Microspheres

Compared to OCAOCT20-5FL and OCACET20-5FL microspheres, OCAM20-5FL appeared to have a smoother surface. Since these microspheres were prepared using the same experimental conditions, the morphology difference of the microspheres can be attributed to the different alkyl ester groups present. That is, microspheres prepared from long chain ester derivatives had a rougher surface than those made from methyl ester.

The mean particle size diameter of the microspheres is listed in Table 2.

TABLE 2

Average Particle Size of 5-Florouracil Microspheres

| Sample | Average Diameter (μm) | STDV |
|---|---|---|
| OCAM20-5FL | 94.60 | 26.53 |
| OCAOCT20-5FL | 88.64 | 23.21 |
| OCACET-5FL | 150.67 | 32.30 |

In Vitro Dissolution Study

The dissolution of the three 5-FU microsphere formulations was performed in pH 7.4 PBS buffer at 37.0° C. under sink conditions. The solubility of 5-fluorouracil in pH 7.4 phosphate buffer saline solution was determined to be 14.86 mg/ml. OCAM20-5FL microspheres released 100% drug in about 550 hours. The release of 5-FU from OCAOCT20 and OCACET20 microspheres was slower (90% in 1500 hours) and occurred in a biphasic manner. This was attributed to the intrinsic properties of the polymer. The internal structure of OCAM20 did not change significantly before and after release (500 hours), while more pores were observed after 1500 hours release for OCAOCT20 microspheres.

Release Mechanism Study

The release data of OCA ester microspheres were analyzed using a polymer degradation release model, as shown below:

$$\ln\left(\frac{X}{1-X}\right) = kt + m$$

In this equation, X is the fraction of drug released at time t, k is a rate constant and m is a constant. In the release profile of OCAM20, the first several data points were due to the burst release of drug crystals near the surface. After 80 hours, the release data was fitted to the Model above using JUMPIN®. The R square of the fitting is 0.9913, indicating the release of 5-fluorouracil follows polymer degradation release mechanism.

Example 4

Preparation of Oxidized Cellulose Acetate Alkyl Ester

Methods

Oxidized cellulose acetate (OCA) was prepared from oxidized cellulose (OC) by treatment with a mixture of $Ac_2O$/$HAC$/$H_2SO_4$. The methyl and ethyl esters of OCA (OCAM and OCAE, respectively) were prepared by reacting OCA with methanol or ethanol using dicyclohexylcarbodiimide and dimethylaminopyridine as the catalysts. The new esters were characterized by FT-IR, $^1H$ and $^{13}C$ NMR, $^1H$-$^{13}C$ HQMC NMR, and powder X-ray diffraction methods. The weight loss studies on OCA were performed in pH 7.4 phosphate buffer-saline (PBS).

Results

The yields of OCAM and OCAE ranged from 45% to 78, respectively. The carboxylic acid contents (w/w) of OCAM and OCAE were 1.35, and 0.97%, respectively. The moisture contents determined by drying over $P_2O_5$ were 2.16 and 1.36%, respectively. The IR and NMR spectra showed peak patterns conforming to the structures of OCAM, and OCAE.

Conclusions

Results show that OC can be converted into ester derivatives for potential applications as biodegradable polymers in drug delivery and related areas.

Example 5

Characterization of Alkyl Esters of Oxidized Cellulose Acetate (OCAM and OCAE)

The OCAM and OCAE prepared in Example 2 were characterized as follows.

Carboxylic Acid Content Determination

The carboxylic acid content was determined according to the USP methods (USP 26: Acid value determination, 391; Oxidized cellulose, 2068).

Fourier-Transform Infrared (FT-IR) Spectroscopy

The FT-IR spectra were obtained on a Nicolet 210 infrared spectrophotometer (Nicolet Instruments Corporation, Madison, Wis., USA), equipped with Omnic software.

Proton and Carbon-13 Nuclear Magnetic Resonance ($^1H$-NMR and $^{13}C$-NMR) Spectroscopy The $^1H$- and $^{13}C$-NMR spectra of samples were measured in dimethylsulfoxide-d6 (DMSO-$d_6$) or chloroform-d (CDCl$_3$) on a Bruker MSL-360 NMR spectrometer.

Powder X-Ray Diffractometry (PXRD)

The powder X-ray diffraction (XRD) measurements were conducted on a Siemens Model D5000 diffractometer using monochromatic CuKα (α1=1.54060°) rays and a step width of 0.02° 2θ/min. over an angular range of 5-40° 2θ with a time constant of 0.5 S. The X-ray data were processed by Diffrac$^{Plus}$ diffraction software (EVA, version 2.0, Siemens Energy and automation, Inc. Madison, Wis.).

Apparent Ionization Constant of OC and OCA

The apparent pKa of OC and OCA-14 was determined using the general Henderson-Hasselbach equation, pKa=pH+ nlog {(1−α)/α, where a is the degree of ionization of the polyacid calculated using the relationship: α=1−[{H−B−P}/P], where H is the total number of milliequivalent of acid added, B is the number of milliequivalent of base used to dissolve the polymer prior to titration, and P is the milliequivalent of acid in the sample used.

Moisture Content Determination

The moisture content was determined using a Perkin Elmer Thermogravimetric Analyzer (TGA 7, temperature range: 25-200° C.; heating rate: 10° C./min), or by drying the sample over $P_2O_5$ to a constant weight.

Intrinsic Viscosity and Molecular Weight of OCA

The intrinsic viscosity, [η], and the viscosity-average molecular weight of the polymer were determined in acetone at 20.0±0.1° C. using a Canon-Fenske capillary viscometer (size 50) according to the relationship: [α]=$K_m M^α$, where $K_m$ and a are constants. For cellulose acetate, in acetone, $K_m$ is $2.31\times10^{-5}$ dl/g and a is 1. [η] was calculated from the equations:

$$\frac{\eta_{sp}}{C} = [\eta] + K'C \text{ and } \frac{\ln\eta_{red}}{C} = [\eta] - K''C,$$

where, $\eta_{sp}=\eta_{rel}-1$, $\eta_{rel}=t/t_0$, t and $t_0$ are the efflux times for the sample solution and blank solvent, respectively, and C is the concentration of sample in g/dl.

Results and Discussion

The notable features in the IR spectra of OCA-14, OCAM, and OCAE, compared to that of OC-14, are: (1) a strong band at 1750 cm$^{-1}$ due to ν(C=O) vibration of the ester group (the band masks the peak due to ν(C=O)COOH, which appears at 1734 cm$^{-1}$); (2) two bands at 1060 and 1240 cm$^{-1}$ due to ν(C—O); and (3) the reduced intensity of the broad peak in the region between 2500-3500 cm$^{-1}$, centered at 3481 cm$^{-1}$, due to ν(O—H) vibration. (FIG. 1).

Figure 2:
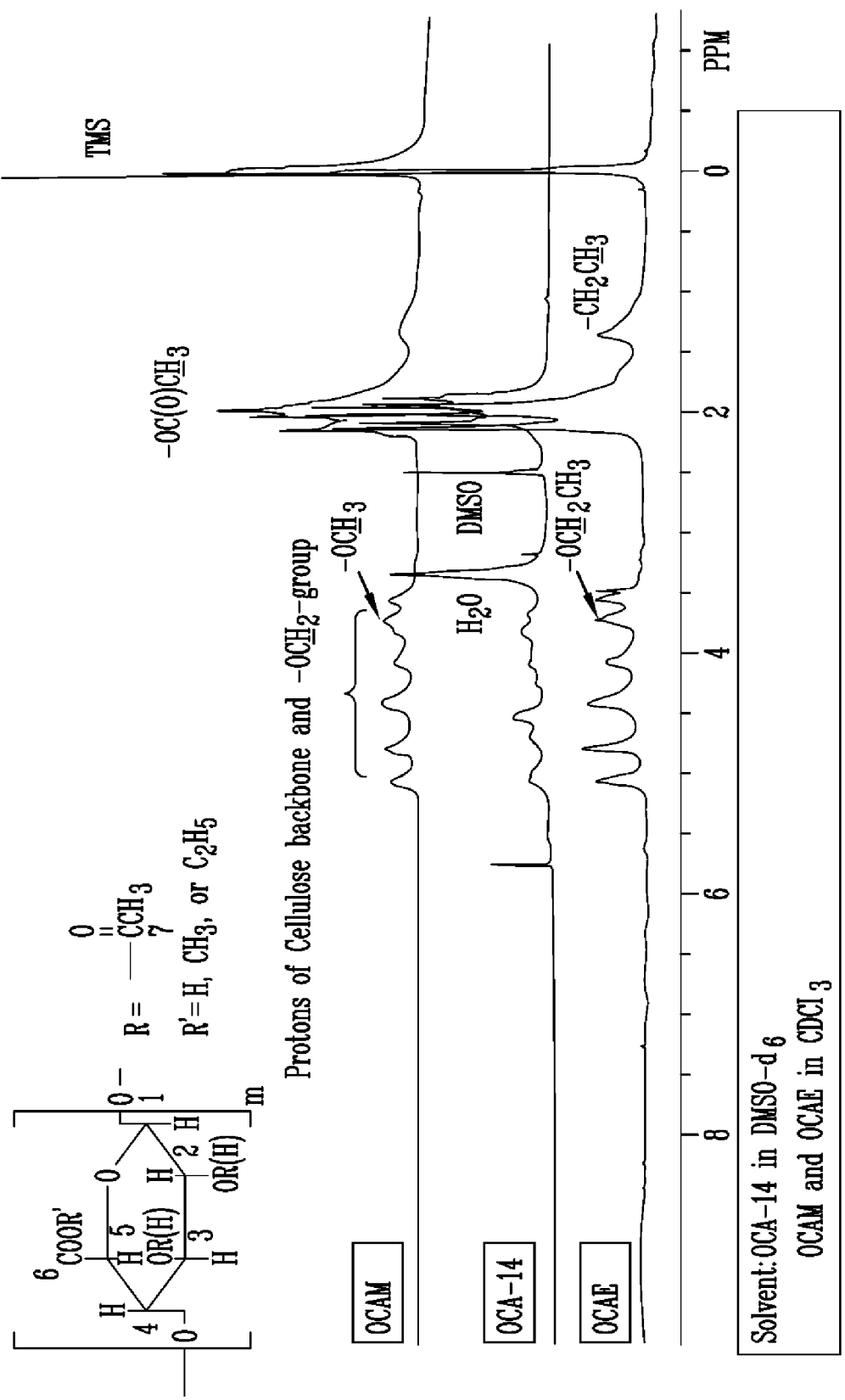
FIG. 2 shows the $^1$H-NMR spectra of OCA-14 (DS=2.2), OCAM-14, and OCAE-14, as described in Example 5.

In the $^1$H-NMR spectra, anhydrous glucose backbone protons appear at 3.5 ppm~6.0 ppm, and protons from acetyl groups at 1.5 ppm~2.3 ppm. The protons from $CH_3O$— and —$CH_2O$— occur at ~3.7 ppm (FIG. 2).

Figure 3:
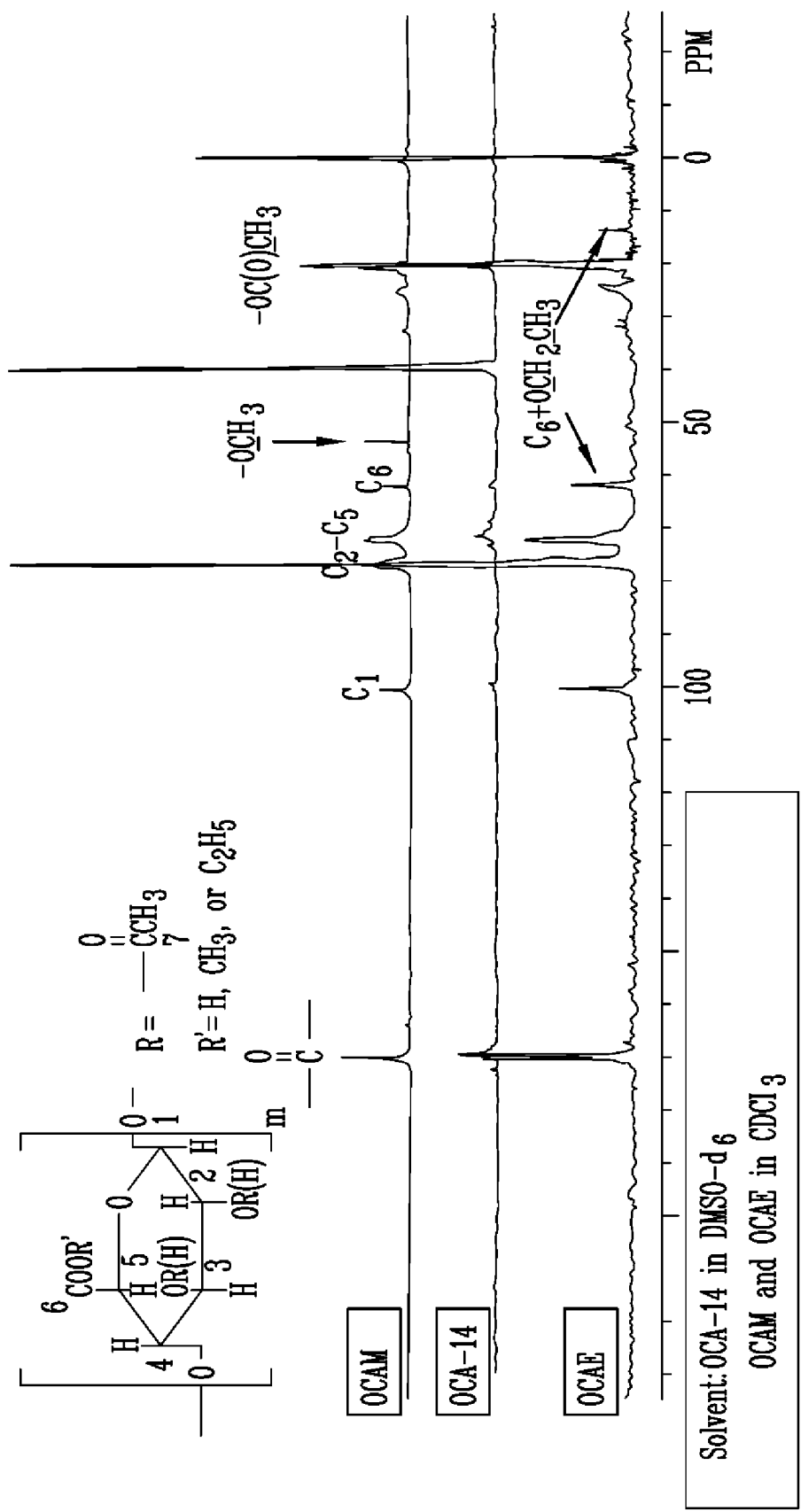
FIG. 3 shows the $^{13}$C-NMR spectra of OCA-14 (DS=2.2), OCAM-14, and OCAE-14, as described in Example 5.

In the $^{13}$C-NMR spectra, the peaks at 100.4, 71.7, 72.4, 72.7, 76.0, and 63.4 ppm are attributed to C1, C2, C3, C4, C5, and C6, respectively. The peak at ~170 ppm is due to carbonyl carbons belonging to the acetyl and carboxyl acid groups. The peaks at 53.4 ppm and 61.3 ppm belong to $CH_3O$— and —$CH_2O$— carbons. The methyl carbon in ethyl group is identified at 14.1 ppm (FIG. 3).

Figure 4:
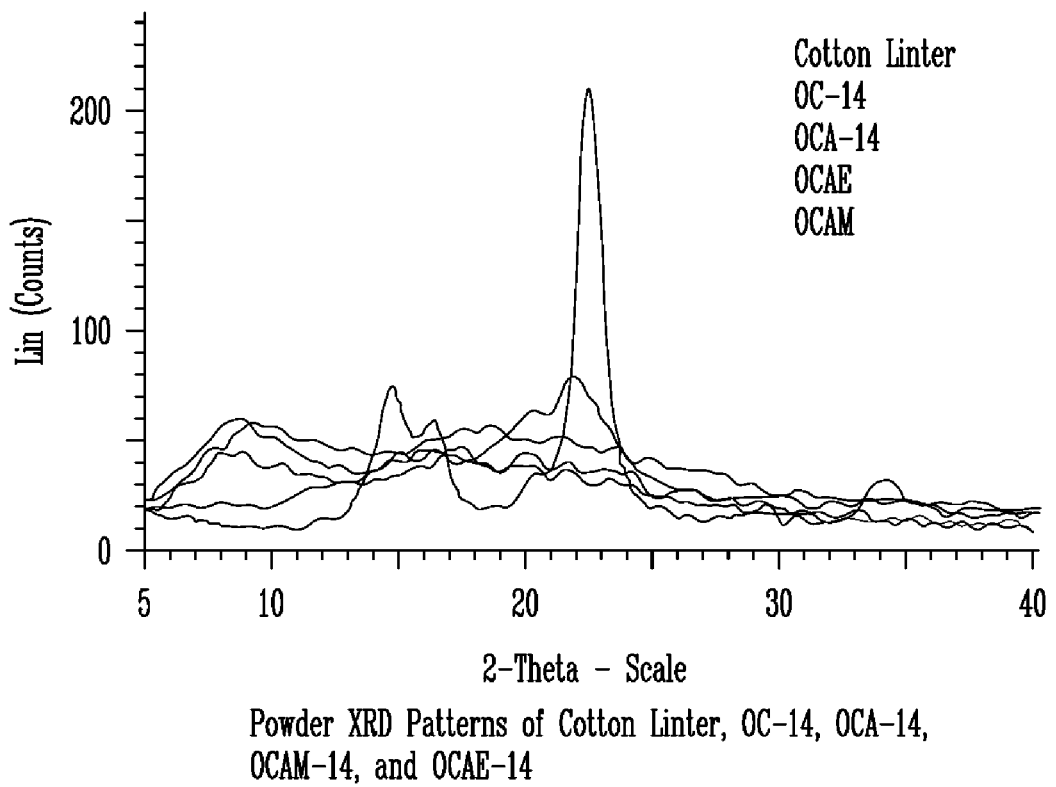
FIG. 4 shows the powder X-ray diffraction patterns of cotton linter, OC-14, OCA-14, OCAM-14, and OCAE-14, as described in Example 5.

Compared to cotton linter and OC (the starting material), OCA-14, OCAM and OCAE are nearly amorphous materials. (FIG. 4).

OCA-14, OCAM, and OCAE are soluble in common organic solvents. OC, in contrast, can only be dissolved in alkaline aqueous solutions. See Table 3 below:

TABLE 3

Solvent Systems for OC and Its Alkyl Acetate Esters

| Solvents | Polymer | | |
|---|---|---|---|
| | OC-14 | OCA-14 | OCAM-14 |
| Water | X | X | X |
| Acetone | X | √ | √ |
| Methylene dichloride | X | X | √ |
| Ethyl acetate | X | X | X |
| DMF | X | √ | √ |
| DMSO | X | √ | √ |

√ = soluble
X = insoluble

Figure 5:
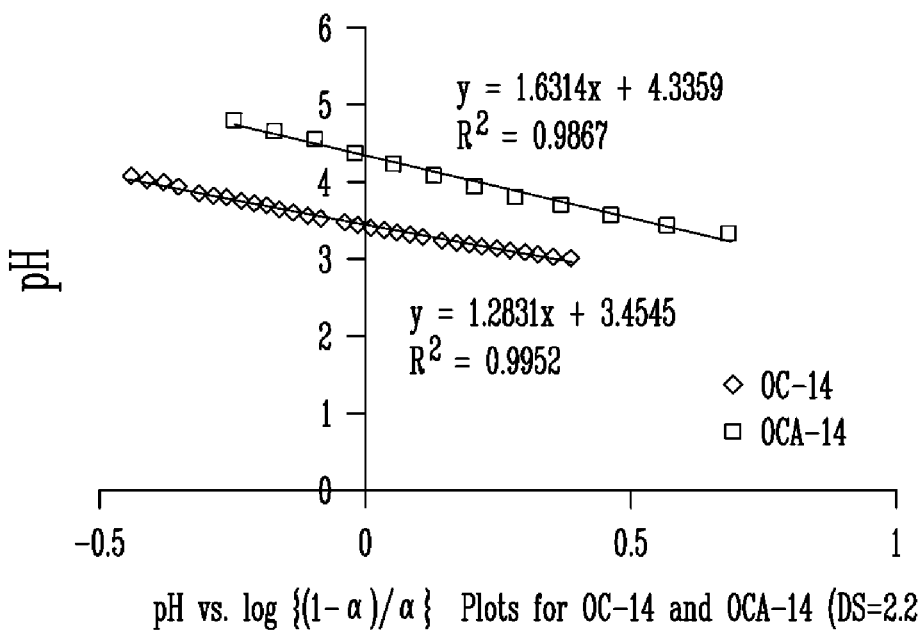
FIG. 5 shows the pH vs. log $\{(1-\alpha)/\alpha\}$ plots for OC-14 and OCA-14 (DS=2.2), as described in Example 5.

The apparent pKa of OC-14 and OCA-14 are 3.45 and 4.34, respectively. (FIG. 5). The moisture content of the compounds are set forth in Table 4.

TABLE 4

Moisture Content of OC-14, OCA-14, OCAM-14, and OCAE-14

| Sample | TGA (%)(n = 3) | $P_2O_5$ (%)(n = 3) |
|---|---|---|
| OC-14 | 10.8 (±0.14) | — |
| OCA-14 | — | 8.92 (±0.32) |
| OCAM-14 | 1.74 (±0.62) | 2.16 (±0.09) |
| OCAE-14 | 1.05 (±0.02) | 1.36 (±0.09) |

The carboxylic acid contents in OCAM and OCAE are significantly reduced compared to OC and OCA, indicating the substitution of carboxylic acid groups by methyl and ethyl esters, as shown in Table 5.

TABLE 5

Carboxylic Acid Content of OC-14, OCA-14, OCAM-14, and OCAE-14

| Sample | Carboxylic Acid Content (%) |
|---|---|
| OC-14 | 14.00 |
| OCA-14 | 10.60 |
| OCAM-14 | 1.35 |
| OCAE-14 | 0.97 |

Figure 6:
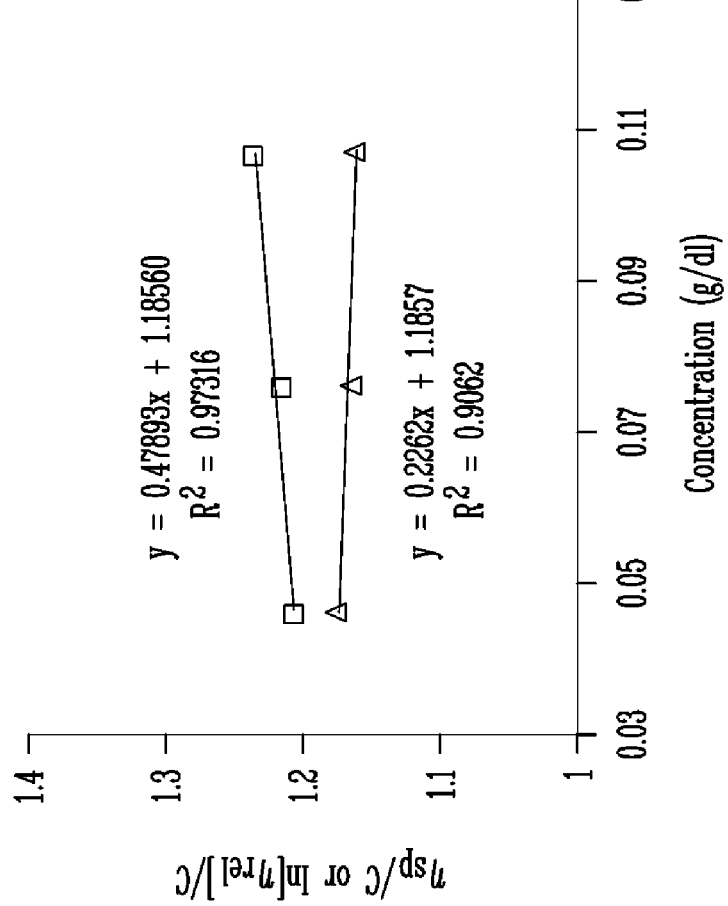
FIG. 6 shows the intrinsic viscosity and molecular weight measurement of OCA-14, as described in Example 5.

The average viscosity molecular weight of OCA-14 is about 50,000, corresponding to the degree of polymerization (DP) of 194. The molecular weight of OCAM and OCAE were not determined, but they are expected to have the same molecular weight (~50,000) because of the mild non-hydrolyzing reaction condition used in their preparation. (FIG. 6).

Conclusions

OCA can be prepared from OC by treatment with $Ac_2O$/ $HOAc/H_2SO_4$. The preparation of OCAM and OCAE can be achieved from reaction between OCA and MeOH or EtOH in the presence of DCC and DMAP.

OCA and its methyl/ethyl esters are soluble in commonly used organic solvents.

Compared to cellulose, OCA and its methyl and ethyl esters are low crystallinity materials. (FIG. 6).

The apparent pKa of OC-14 and OCA-14 are 3.5 and 4.3, respectively (FIG. 3).

The viscosity average molecular weight of OCA-14 is about $5.13\times10^4$, which corresponds to a degree of polymerization (DP) of 194.

Example 6

Preparation of Sustained-Release Microsphere Formulations of Camptothecin Using New Biodegradable Oxidized Cellulose Esters Purpose To develop microsphere formulations of camptothecin (CPT), a highly potent antineoplastic agent, using oxidized cellulose acetate (OCA) and oxidized cellulose methyl (OCAM) esters.

Methods

OCA was prepared from oxidized (OC, COOH content 14% w/w) by treatment with a mixture of $Ac_2O$/HOAC/$H_2SO_4$. The preparation of OCAM was achieved from a reaction between OCA and methanol using dicyclohexylcarbodiimide and 4,4'-dimethylaminopyridine as the catalysts. OCA and OCAM microspheres containing CPT were prepared by the emulsion/solvent evaporation method using the $CH_2Cl_2$—$CH_3OH$ mixture as a solvent and polyvinyl alcohol as an emulsifier. Microspheres were characterized by IR, scanning electron and confocal microscopes, and powder X-ray diffractometry. Dissolution studies were performed in pH 7.4 phosphate buffer-saline (PBS) at 37° C.

Results

OCA-CPT microspheres ranged in size 86±31 μm and showed discontinuous and rough surfaces. OCAM-CPT microspheres, compared to those made using OCA, were smaller in size (68±17 μm) and had smoother surfaces. The drug loading efficiencies for OCA and OCAM microspheres were 46-76% and 100%, respectively. OCA microspheres with low CPT loading showed a diffused XRD pattern, whereas those with high CPT loading displayed the presence of small amounts of crystalline CPT. The dissolution of CPT in pH 7.4 PBS followed the following order: free CPT>OCA-CPT (CPT 2.3%)>OCA-CPT (CPT-6.6%)>OCAM-CPT (CPT 8.6), with the $t_{1/2}$ values corresponding to 6, 12, 30, and 1500 hours, respectively. The HPLC analyses of OCA-CPT and OCAM-CPT microspheres, after 4 weeks of storage in pH 7.4 PBS, showed the presence of the CPT-lactone form in the microspheres, suggesting that both OCA and OCAM have the stabilizing effect on CPT. Both OCA and OCAM slowly degrade in pH 7.4 PBS.

Conclusions

Results demonstrate that the new OCA esters can be used to prepare biodegradable sustained-release microsphere formulations.

Example 7

Preparation and Characterization of OCA-CPT and OCAM-CPT Microspheres

Purpose

To develop microsphere formulations of camptothecin (CPT), a highly potent antineoplastic agent, using oxidized cellulose acetate (OCA) and oxidized cellulose methyl (OCAM) esters.

Methods

OCA was prepared from oxidized (OC, COOH content 14% w/w) by treatment with a mixture of $Ac_2O$/HOAC/$H_2SO_4$. The preparation of OCAM was achieved from a reaction between OCA and methanol using dicyclohexylcarbodiimide and 4,4'-dimethylaminopyridine as the catalysts. OCA and OCAM microspheres containing CPT were prepared by the emulsion/solvent evaporation method using the $CH_2Cl_2$—$CH_3OH$ mixture as a solvent and polyvinyl alcohol as an emulsifier. Microspheres were characterized by IR, scanning electron and confocal microscopes, and powder X-ray diffractometry. Dissolution studies were performed in pH 7.4 phosphate buffer-saline (PBS) at 37° C.

```
CPT
 │ CH2Cl2:CH3OH (4:1)
 ▼
CPT suspension/solution
   in                              1% PVA solution
CH2Cl2—CH3OH                       in water
 │                                    │
 │ OCA or OCAM                        │ Stir at 400 r.p.m.
 ▼                    Add             ▼
CPT suspension/solution    ──────►  O/W emulsion
  + polymer solution in                │
CH2Cl2—CH3OH                          │ 200 r.p.m.
                                       ▼
                         Microspheres ──────► Filter & dry
```

Characterization Methods

Scanning Electron Microscopy (SEM): SEM photographs were taken on a Hitachi S-4000 scanning electron microscope (Hitachi Ltd., Tokyo, Japan) with an Emitech K550 coater (Emitech Products, Inc, Houston, Tex.).

Confocal Microscopy: Fluroescence photographs were taken using a Bio-Rad 600 confocal scanning system, equipped with an argon-krypton laser. The excitation and emission wavelengths used were 488 nm and 515 nm, respectively.

Mean Diameter of Microspheres: The mean diameter was measured from SEM photos using EDS200 version 2.9 microanalysis system (IXRF, Ltd., Houston, Tex. 77057).

Powder X-ray Diffractometry (PXRD): PXRD measurements were conducted on a Siemens Model D5000 diffractometer using monochromatic X-rays (Cu Kα1=1.54060 Å) and a step width of 0.020° 2θ/min. over an angular range of 5-40° 2θ with a time constant of 0.5 second. The X-ray data were processed by Diffrac$^{Plus}$ diffraction software (EVA, Version 2.0, Siemens Energy and Automation, Inc., Madison, Wis.).

Analysis of Campthothecin—HPLC

HPLC system: Shimadzu SIL 10A

Detector: RF-551 Fluorescence $\lambda_{Excitation}$=370 nm $\lambda_{Emission}$=435 nm Mobile Phase: 0.1 $Et_3HN$=OAC-buffer (pH 5.4):$CH_3CN$ (73:27)

Column: Supelco Discovery $C_{18}$ (15 cm×4.6 cm, 5 mm)

Drug Content and Drug Loading Efficiency

2~3 mg of microspheres were accurately weighed and dissolved in dimethyl sulfoxide (DMSO). The solution was diluted to 25 ml with the same solvent. 1.0 ml of this solution was removed and diluted to 50 ml with the mobile phase. This diluted solution was then analyzed by HPLC. The drug content and drug loading efficiency were calculated using the following equations:

$$\text{Drug content (\%)} = \frac{\text{CPT determined in sample}}{\text{Weight of sample}} \times 100$$

$$\text{Drug Loading Efficiency (\%)} = \frac{\text{Measured drug content (\%)}}{\text{Theoretical drug content (\%)}} \times 100$$

Release Studies

The release studies were performed under the sink condition in pH 7.4 PBS buffer at 37.0±0.2° C. At predetermined time intervals, 5.0 ml of the release medium was withdrawn. This was immediately replaced with an equal volume of the fresh PBS solution. The removed release medium was appropriated diluted with the mobile phase and analyzed by HPLC.

Results and Discussion

Figure 7:
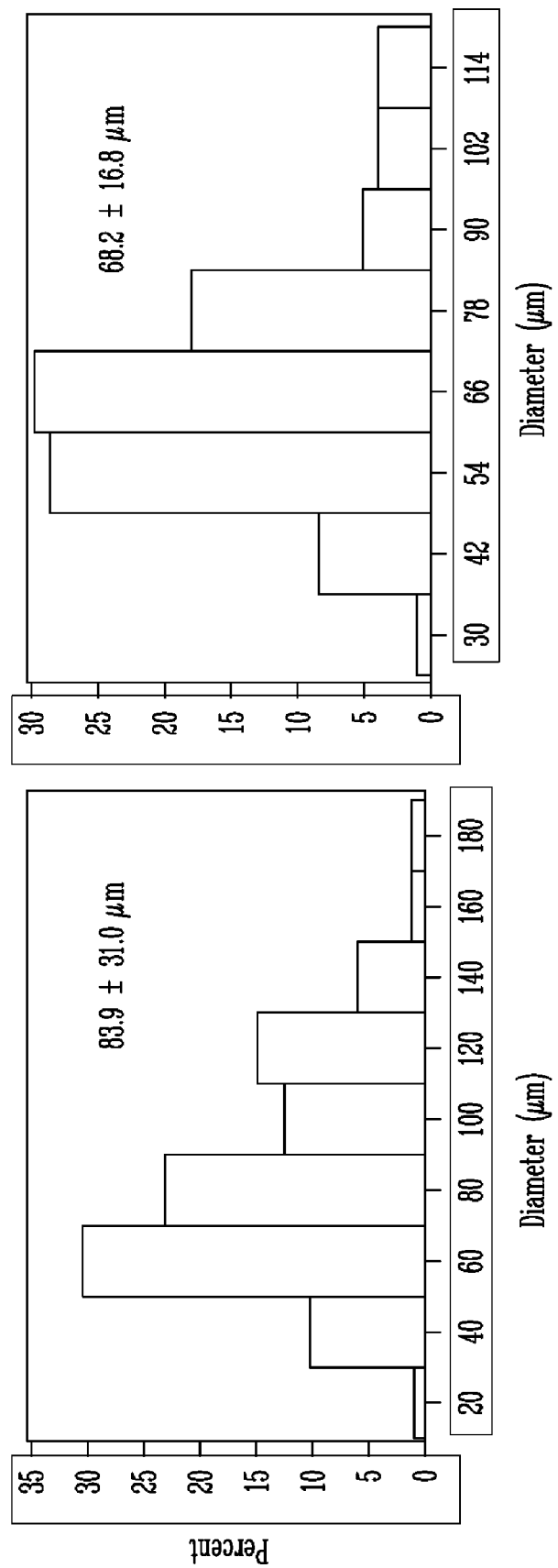
FIG. 7 shows the histograms of diameter distribution of CPT microspheres, as described in Example 6.
Figure 8:
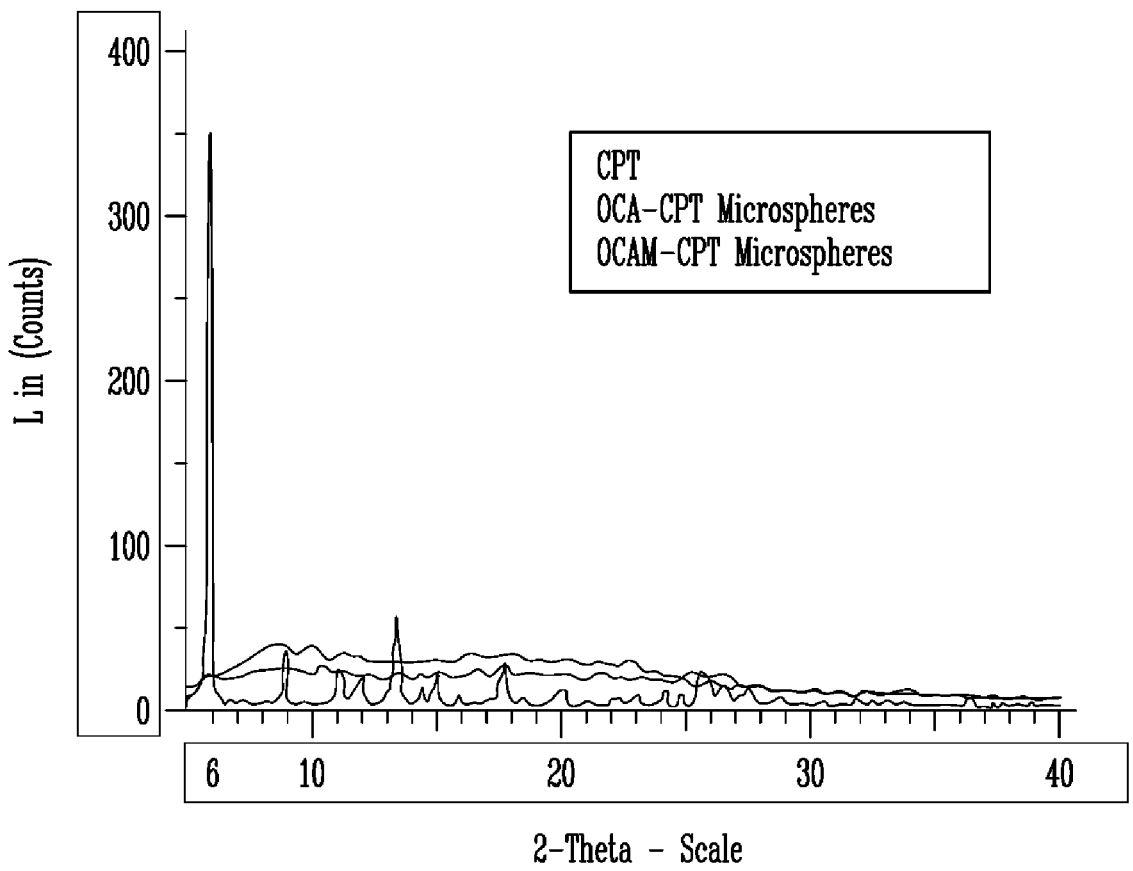
FIG. 8 shows the powder X-ray diffraction patterns of CPT, OCA-CPT, and OCAM-CPT microspheres, as described in Example 6.

Compared to OCA-CPT microspheres, OCAM-CPT microspheres appeared more spherical and showed smoother surface;

Confocal micrographs indicate the uniform distribution of CPT in the microspheres;

The mean diameters of OCAM-CPT and OCA-CPT microspheres were 68.2+16.8 μm and 83.9±31.0 μm, respectively (FIG. 7);

The powder X-ray diffractograms of OCA and OCAM microspheres showed broad diffuse halos, indicating that the drug is present in the amorphous state (FIG. 8);

The CPT contents in the OCA-CPT and OCAM-CPT microspheres were 7.30% and 8.50%, respectively (Table 4), corresponding to the drug loading efficiency of 90.9% and 101.7%, respectively (Table 4).

TABLE 6

Drug Content and Drug Loading Efficiency of OCA-CPT and OCAM-CPT Microspheres

| Sample | Drug Content (w/w, %) | Drug Loading Efficiency (%) |
|---|---|---|
| OCA-CPT | 7.30 (±1.04) | 90.9 (±10.6) |
| OCAM-CPT | 8.50 (±0.127) | 101.7 (±1.36) |

Figure 9:
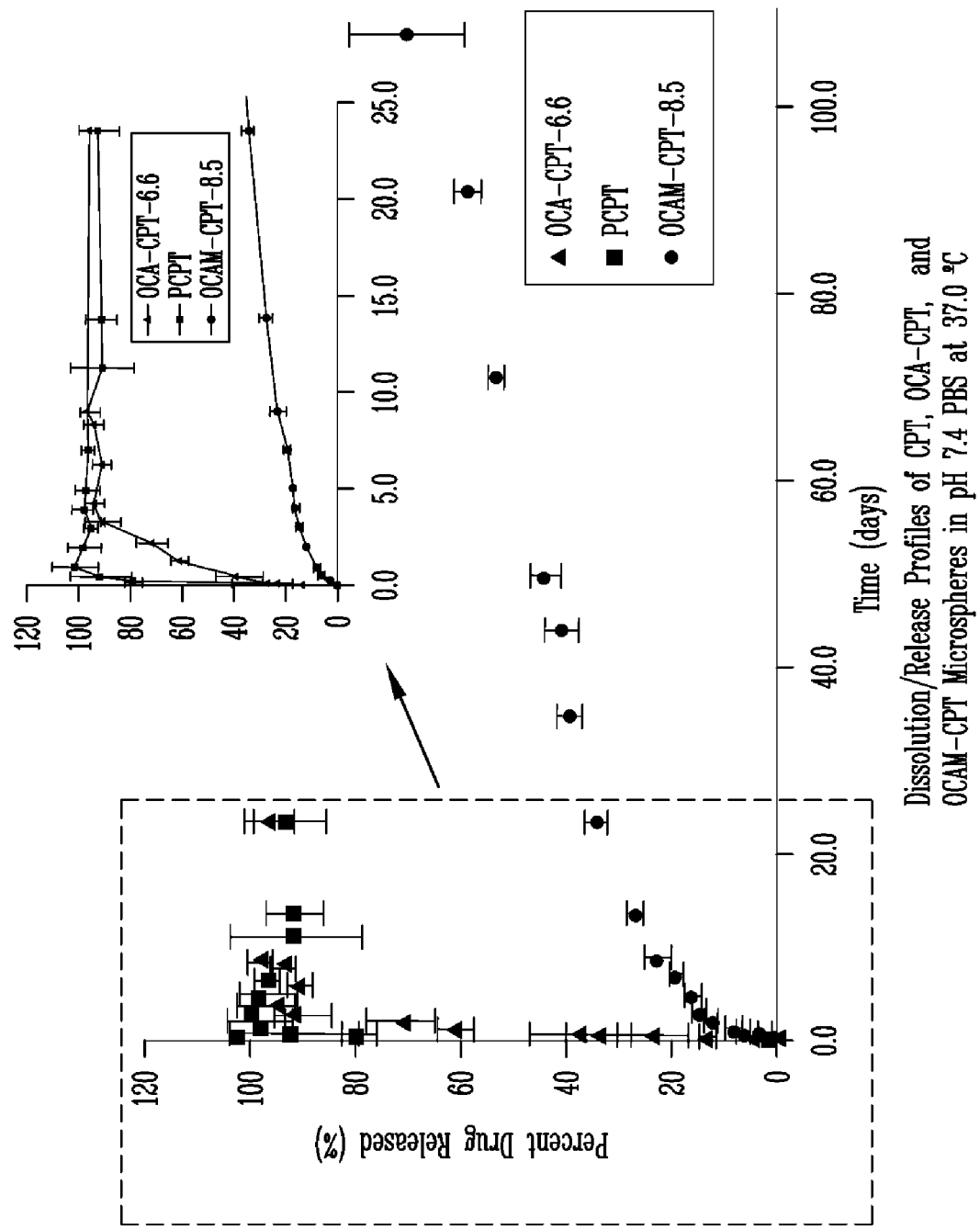
FIG. 9 shows the dissolution/release profiles of CPT, OCA-CPT, and OCAM-CPT microspheres in pH 7.4 PBS at 37.0° C.

Free CPT dissolved in about 48 hours, whereas OCA-CPT microspheres released 100% CPT in about 80 hours (FIG. 9);

OCAM-CPT, in contrast, only released 16% CPT in about 80 hours and about 70% in 100 days (FIG. 9);

The dissolution of CPT in pH 7.4 PBS followed the following order: free CPT>OCA-CPT (CPT 2.3%)>OCA-CPT (CPT-6.6%)>OCAM-CPT (CPT 8.6), with the $t_{1/2}$ values corresponding to 6, 12, 30, and 1500 hours, respectively.

The HPLC analyses of OCA-CPT and OCAM-CPT microspheres, after 4 weeks of storage in pH 7.4 PBS, showed the presence of the CPT-lactone form in the microspheres, suggesting that both OCA and OCAM have the stabilizing effect on CPT. Both OCA and OCAM slowly degrade in pH 7.4 PBS.

Figure 10:
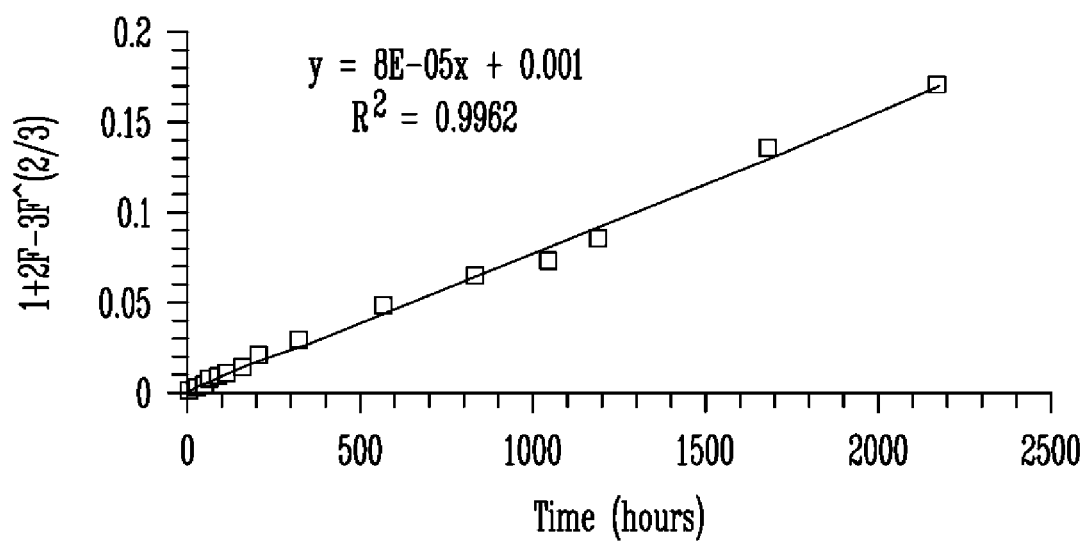
FIG. 10 shows the 1+2F−3(F)^(⅔) model fitting for OCAM-CPT microsphere release.

The CPT release from OCAM-CPT microspheres followed the granular spherical pellet release model (FIG. 10):

$$1 + 2(F) - 3(F)^{2/3} = Kt$$

where, $F = (a/a_0)_3$ = fraction of drug remaining or undissolved; $a_0$ = radius of the microsphere; a = radius of that part of the microsphere still holding drug; and t = time;

Blank OCAM microspheres when placed in pH 7.4 PBS buffer at 37.0° C. for 30 days developed pores on the surface, suggesting that the OCAM degrades at the physiological pH.

Conclusions

OCA and its alkyl/aryl esters, a new class of biodegradable polymers, can be used to prepare microspheres containing camptothecin (CPT) by the conventional emulsion/solvent evaporation method. This method allows uniform distribution of CPT in the microspheres with loading efficiency up to 90-100%.

The presence of a diffuse halo in the powder X-ray diffractograms of the microspheres indicated that the drug exists in the amorphous state.

Although both OCA and OCAM microsphere formulations showed the sustained release of CPT, the release of CPT from OCAM was of longer duration than OCA. In 100 days, 70% of CPT released from the OCAM microspheres.

It should be appreciated that minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A biodegradable, oxidized cellulose carboxylated alkyl/aryl ester (OCCAE) having one of the following general formulas I or II, the general formula:

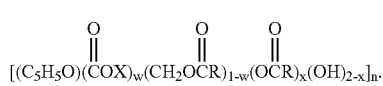

I wherein:

X is H, alkyl ($C_1$-$C_{16}$) or an aryl group;

R is H; $CF_3$; $(CH_2)_n CH_3$, where n is from 0 to 18; $(CH_2)_n$COOH, where n is from 1 to 8; CY=CZCOOH, where Y and Z are independently selected from the group consisting of hydrogen, methyl, branched alkyl having from 1 to 20 carbon atoms and from one to three cis or trans double bonds; branched alkenyl having from 1 to 20 carbon atoms and having from one to three cis or trans double bonds; CY=$CH_2$, where Y is H, methyl, or phenyl; CH=CHY, where Y is $C_6H_5$; CH=CYCOOH, where Y is H or $CH_3$; $(CH_2)_8 CH=CH(CH_2)_8 CH_3$; or $C_6H_{(2-6)}(COOH)_{0-4}$, $CH_2CH(COOH)CH_2$—COOH;

w, is 0.1-1.0;

x is 0.1-2.0; and n is 30-1500;

and

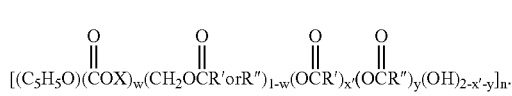

II wherein:

X is H, alkyl ($C_1$-$C_{16}$) or an aryl group;

R' and R" are each selected from the group consisting of: H; $CF_3$; $(CH_2)_n CH_3$, where n is from 0 to 18; $(CH_2)_n COOH$, where n from 1 to 8; $CY=CZCOOH$, where Y and Z are independently selected from the group consisting of hydrogen, methyl, branched alkyl having from 1 to 20 carbon atoms and from one to three cis or trans double bonds; branched alkenyl having from 1 to 20 carbon atoms and having from one to three cis or trans double bonds; $CY-CH_2$, where Y is H, methyl, or phenyl; $CH=CHY$, where Y is $C_6H_5$; $CH=CYCOOH$, where Y is H or $CH_3$; $(CH_2)_8 CH=CH(CH_2)_8 CH_3$; or $C_6H_{(2-6)}(COOH)_{0-4}$, $CH_2CH(COOH)CH_2-COOH$;

w is 0.1-1.0;

x' is 0.1-1.9;

y is 0.1-1.9; and n is 30-850.

2. An OCCAE according to claim 1 that is present in a product selected from the group consisting of a pharmaceutical, an agricultural product, and a veterinary composition.

3. An OCCAE according to claim 1 that is soluble in at least one solvent selected from the group consisting of water, ketones, esters, glycol ethers, glycol ether acetates, alcohols, methylene chloride, halogenated solvents, and aprotic solvents.

4. An OCCAE according to claim 3 whereby the aprotic solvents are selected from the group consisting of DMSO, DMA, DMF, and n-methyl-2-pyrrolidone.

5. A pharmaceutical comprising the OCCAE of claim 1.

6. The pharmaceutical of claim 5 comprising microspheres.

7. The pharmaceutical of claim 6 comprising controlled release microspheres.

8. The pharmaceutical of claim 6 further comprising a drug.

9. The pharmaceutical of claim 8 comprising drug that is released over a time period of between about 150 days to 6 months or longer.

10. The OCCAE according to claim 1 having one of the following general formulas I or II the general formula:

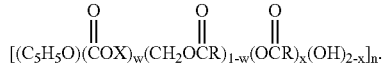

whereby R is H; $CF_3$; $(CH_2)_n CH_3$, where n is from 0 to 5; $(CH_2)_n COOH$, where n is from 2 to 4; R' and R" are each selected from the group consisting of: H; $CF_3$; $(CH_2)_n CH_3$, where n is from 0 to 2; $(CH_2)_n COOH$, where n from 2 to 4; and

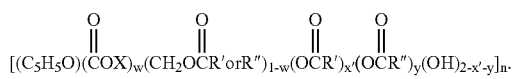

wherein:

R' and R" are each selected from the group consisting of: H; $CF_3$; $(CH_2)_n CH_3$, where n is from 0 to 2; $(CH_2)_n COOH$, where n from 2 to 4.

11. A pharmaceutical comprising the OCCAE of claim 1, said pharmaceutical comprising microspheres.

12. The pharmaceutical of claim 11 comprising controlled release microspheres.

13. The pharmaceutical of claim 11 further comprising a drug.

14. The pharmaceutical of claim 13 comprising drug that is released over a time period of between about 150 days to 6 months or longer.

15. A pharmaceutical comprising: controlled release microspheres comprising at least one oxidized cellulose ester.

16. The pharmaceutical of claim 15 comprising a drug that is released over a time period of between about 24-150 hours.

17. The pharmaceutical of claim 15 comprising from about 1-10% by weight of a drug.

* * * * *

UNITED STATES PATENT AND TRADEMARK OFFICE
CERTIFICATE OF CORRECTION

PATENT NO. : 7,649,089 B2
APPLICATION NO. : 10/975248
DATED : January 19, 2010
INVENTOR(S) : Kumar et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1002 days.

Signed and Sealed this

Twenty-third Day of November, 2010

David J. Kappos
*Director of the United States Patent and Trademark Office*